United States Patent [19]
Bennett et al.

[11] Patent Number: 5,421,548
[45] Date of Patent: Jun. 6, 1995

[54] I.V. STAND AND ATTACHMENTS

[76] Inventors: James R. Bennett, 400 Wilma Cir., Apt. 302, Riviera Beach, Fla. 33404; Marinus Bakels, 3896 Burns Rd., Palm Beach Gardens, Fla. 33410

[21] Appl. No.: 221,884

[22] Filed: Apr. 1, 1994

[51] Int. Cl.⁶ .............................................. A47K 1/04
[52] U.S. Cl. .................................... 248/129; 5/503.1; 248/278; 280/304.1
[58] Field of Search ............... 248/129, 125, 131, 278; 297/DIG. 4; 280/304.5, 304.1, 292; 5/503.1

[56] References Cited

U.S. PATENT DOCUMENTS

| | | | |
|---|---|---|---|
| 4,828,208 | 5/1989 | Peterson et al. | 248/129 X |
| 4,945,592 | 8/1990 | Sims et al. | 248/129 |
| 4,966,340 | 10/1990 | Hunter | 5/503.1 X |
| 5,100,091 | 3/1992 | Pollak | 248/278 |
| 5,219,139 | 6/1993 | Hertzler | 280/304.1 X |
| 5,288,093 | 2/1994 | Gross | 280/304.1 X |

*Primary Examiner*—Ramon O. Ramirez
*Attorney, Agent, or Firm*—Jack N. McCarthy

[57] ABSTRACT

An I. V. stand is provided for (1) use by itself; (2) releasable use with a wheelchair providing for movement of its supporting wheels to provide only swiveling wheels; and (3) use with a gurney providing an adjustable arm attachment. The I. V. pole has an indicator for showing the position of a snubber, or attachment, mechanism used to contact the wheelchair. The I. V. stand has two castered forward wheels and two non-pivoted rear wheels with a castered fifth wheel located between the rear wheels for lifting the rear wheels off a floor when all castered wheels are desired on the I. V. stand.

12 Claims, 8 Drawing Sheets

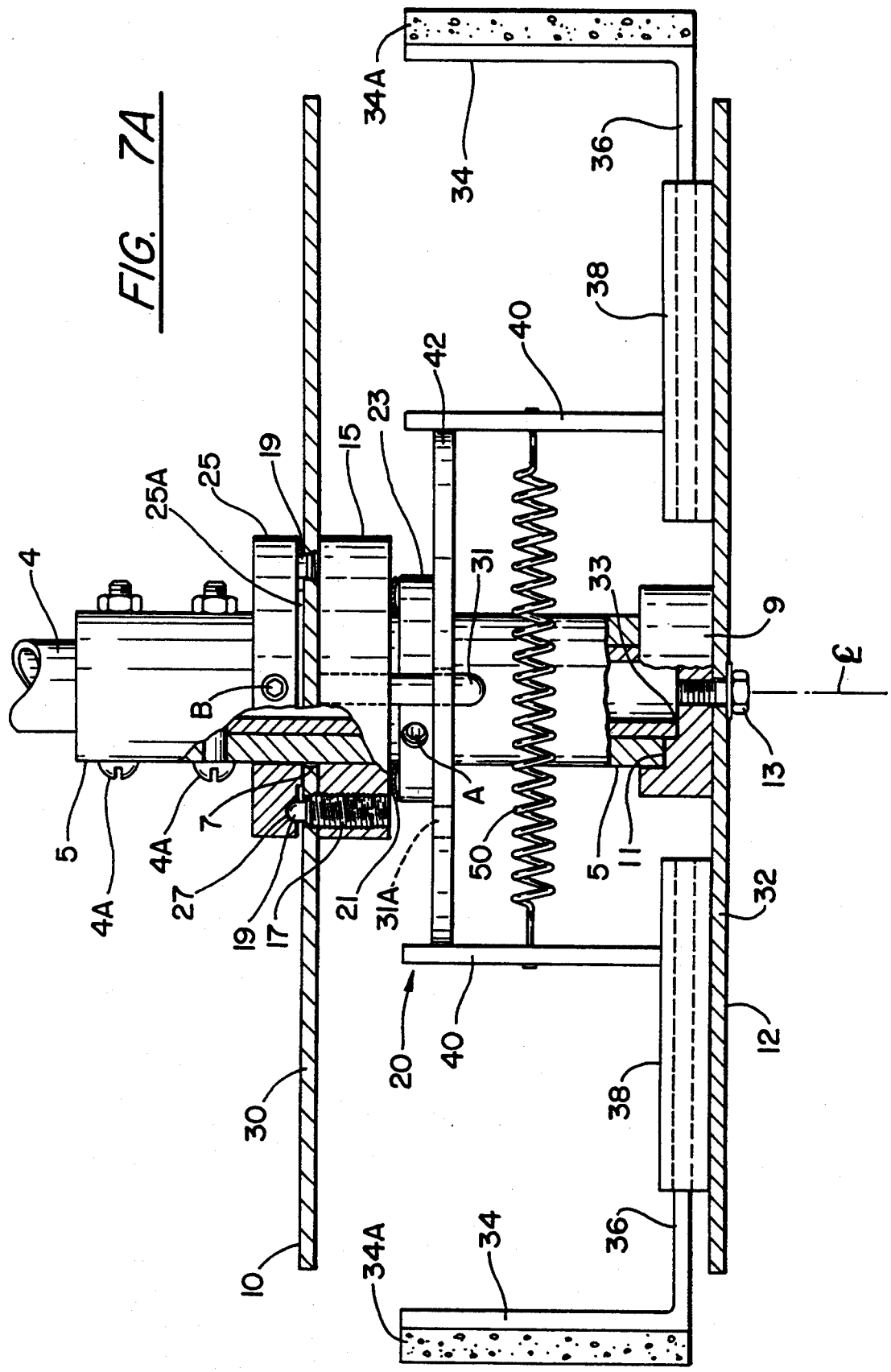

I.V. STAND AND ATTACHMENTS

TECHNICAL FIELD

This invention relates to intravenous stands for use in hanging articles necessary at an elevated position for medical patients, including attachments to wheelchairs, gurneys, etc., and other types of patient conveyances.

BACKGROUND ART

I. V. stands currently have four or more caster wheels mounted to a weighted base for movement in all directions. After a period of time, the casters, for one reason or another, show signs of wear, due mainly to the accumulation of debris, etc. and tend to "fight" each other, thus making the I. V. stands hard to control or to steer. Often when a patient is moved in a wheelchair or other conveyance, a second person is required to move the I. V. stand while the first person moves the conveyance.

The following patents show background for I. V. stand construction and use with wheelchairs: U.S. Pat. Nos. 3,709,556; 4,332,378; 4,511,157; 4,572,536; 4,905,944; and 5,219,139.

DISCLOSURE OF INVENTION

An object of this invention is to provide a means of accurate control of the movement of the I. V. stand and a built-in mechanism to attach it to a wheelchair and/or other types of standard patient conveyances, therefore providing one-person transportation and eliminating the need for the second person.

Another object of this invention is to incorporate a low center of gravity in a flexible chassis to provide a torsion effect to absorb weight transfer and energy. The I. V. pole has many functions beyond the normal uses of holding I. V. bottles, i.e., monitoring equipment. The I. V. pole of this invention provides a suitable means for steering when in a locked forward position. The I. V. pole, when rotated up to 90 degrees, will operate a wheelchair snubber mechanism by extending the sliding snubbers, or holding flanges, to contact a wheelchair's foot bars. A handle on the I. V. pole indicates the position of the snubbers, or holding flanges.

A further object of this invention is to provide a fifth wheel that can be extended and retracted by the use of a suitable device that is foot-operated. The extended fifth wheel raises two rear stationary, non-swiveling, wheels off the floor. The base of the I. V. stand is then riding on three swivel caster wheels through the use of an attachment on the I. V. pole. This permits the I. V. stand to move in any direction when attached to a wheelchair, gurney, or other patient conveyance. Adjustable arms and clamps attach to a patient conveyance, such as a gurney, to provide one-person transporting.

Another object of this invention is to incorporate larger caster wheels on the front and stationary, non-swiveling, wheels on the rear of the base in place of the four or more small caster wheels on currently available I. V. stands. This provides positive tracking and controlled steering. The larger wheels resist stoppage by small objects that tile stand may encounter on floors.

Another object of this invention is to provide a standard diameter pole for the attachment of accessories or other equipment supplies, such as the steering wheel, trays, etc. The pole is a suitable height and is non-adjustable. Adjustable poles can be substituted.

Another object of this invention is to provide a platform on either end of the base to carry oxygen equipment by providing a fence, or other holding device, on the base.

It is another object of this invention, when the I. V. stand is used with a wheelchair, to (1) rotate the I. V. pole to have a snubber mechanism extend to releasably connect itself to a wheelchair and (2) extend a fifth caster wheel on the I. V. stand to provide all swivel wheels contacting the floor.

BRIEF DESCRIPTION OF THE DRAWINGS

FIG. 7A is a view taken on the line 7A—7A of FIG. 6 including the upper plate and the connection of the mounting tube to the upper plate and I. V. pole;

BEST MODE FOR CARRYING OUT THE INVENTION

Figure 1:
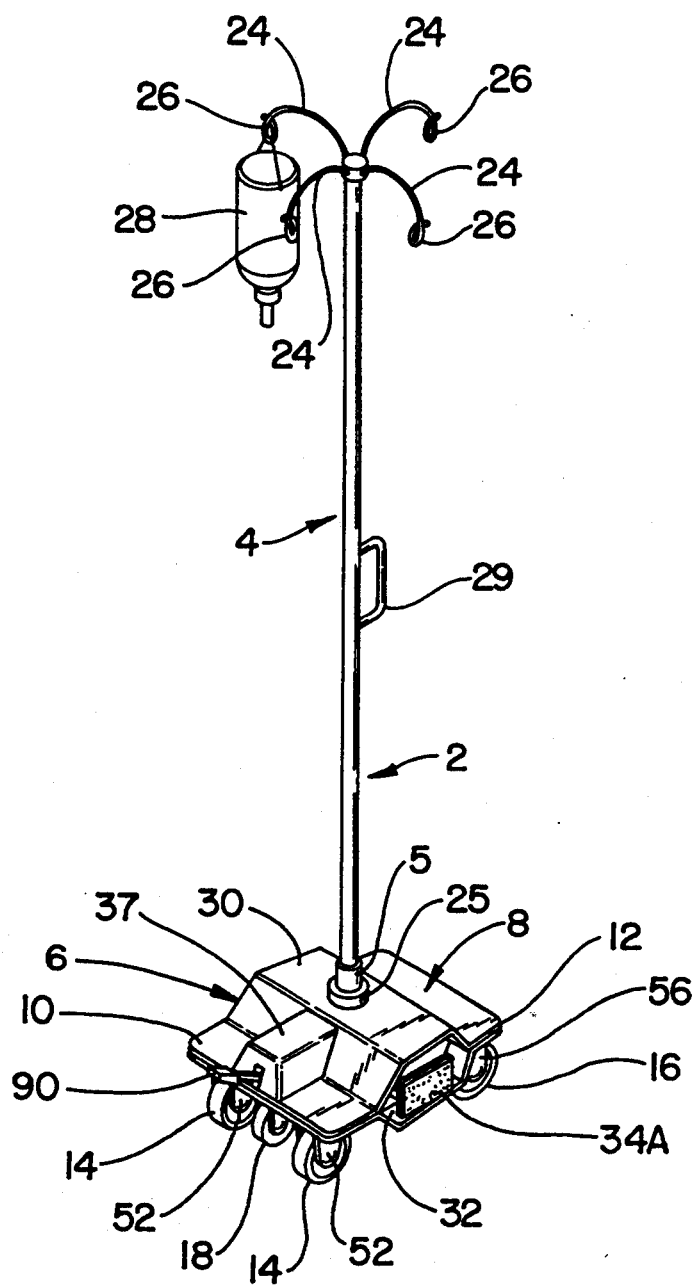
FIG. 1 is a perspective view of the I. V. stand.
Figure 2:
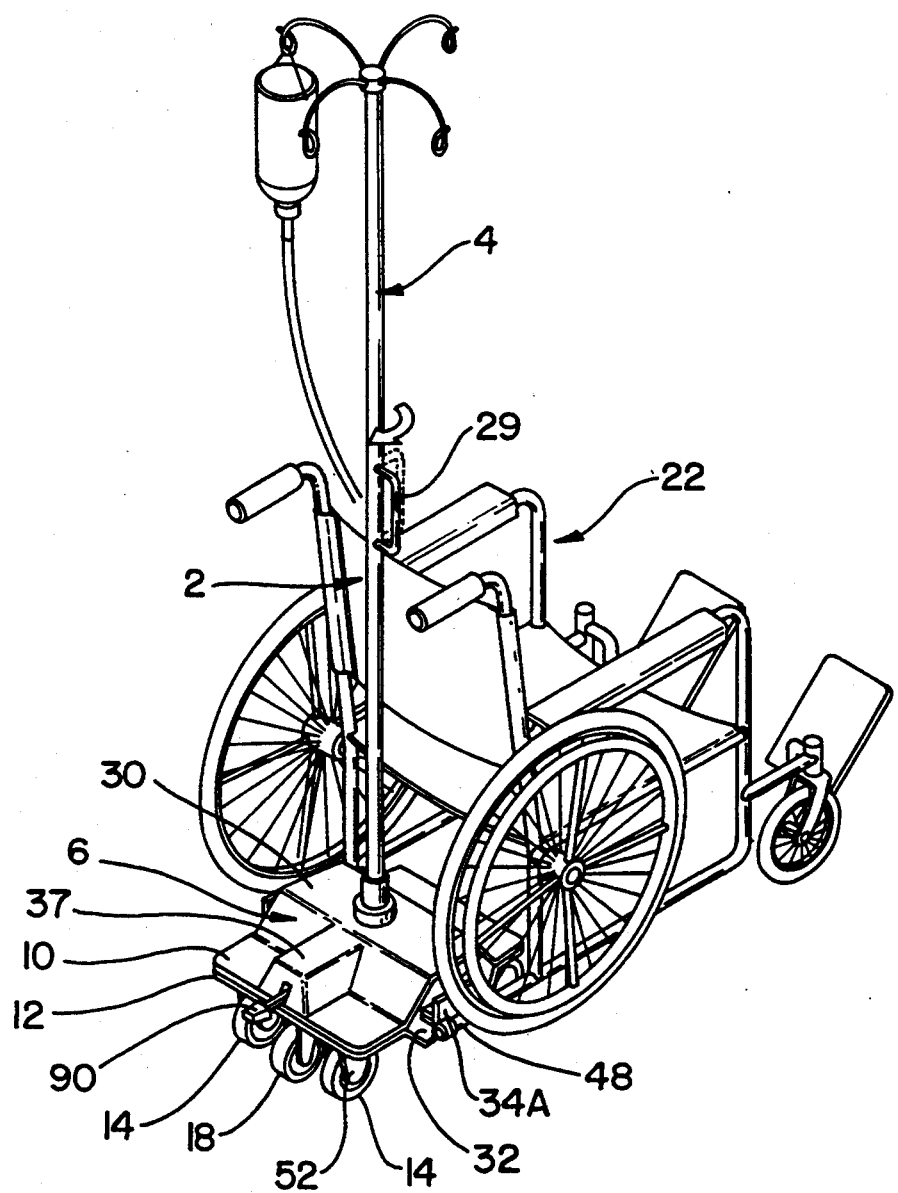
FIG. 2 is a perspective view of the I. V. stand attached to a wheelchair by a snubber, or attachment, mechanism for moving therewith.

As shown in FIG. 1, an intravenous, I. V., stand 2 has two (2) main parts:
(1) a pole 4; and
(2) a base 6. The base 6 has four (4) main parts:
(1) a housing 8 comprising an upper and lower sheet metal plate 10 and 12, respectively, fixed together;
(2) four (4) main wheels mounted on said housing 8; two (2) rearwardly mounted non-pivoted, stationary, wheels 14 and two (2) forwardly mounted pivoted wheels 16 having caster for swiveling;
(3) a foot-operated extendable pivoted wheel 18 mounted between the rearwardly mounted non-pivoted wheels 14; and (4) a snubber, or attachment, mechanism 20 mounted in said housing 8 for attaching said I. V. stand 2 to a wheelchair 22.

The top of the pole 4 has four (4) arms 24 with hook means 26 for connecting intravenous bottles 28, or other devices thereto. One or more hook means 26 can be used.

The bottom of the pole 4 is attached to the base 6 in a manner to be hereinafter described. Upper plate 10 is flat at each end and has a raised portion at the center with angled sides and a flat top 30. Lower plate 12 is flat at each end, matching the flat ends of upper plate 10 and mating therewith, and has a lowered portion at the center with angled sides and a flat bottom 32 under the raised portion of the upper plate 10. The flat ends of upper plate 10 are fixed, such as by bolts, to the flat ends of lower plate 12, with a space being formed between the flat top 30 and flat bottom 32. The snubber, or attachment, mechanism 20 and a mounting tube 5 for pole 4 are positioned in this space.

The I. V. pole 4 is attached to base 6 by being received and fixed in the mounting tube 5 to provide pivotal capability to turn the I. V. pole 4 and mounting tube 5 90° by a handle 29 on the I. V. pole 4 to operate the snubber mechanism 20. Bolts 4A are shown fixing I. V. pole 4 to the mounting tube 5. The handle 29 points forwardly when the snubber mechanism 20 is retracted, and the handle 29 points 90° to the right when the snubber mechanism 20 is fully extended. A clearance hole 7 is provided in upper plate 10 for the top of a mounting tube 5 to extend therethrough. The mounting tube 5 is held in alignment at its lower end by a bottom bushing 9 fixed to lower plate 12 which has a recess 11 to receive the lower end of the mounting tube 5. The I. V. pole 4 extends through the mounting tube 5 and is received in a second recess 33 in the bottom of recess 11. The bottom bushing 9 is fixed to the lower plate 12 by a machine screw 13.

A spring plunger collar 15 is fixedly mounted under the upper plate 10 by machine screws C with a center opening therein aligned with clearance hole 7. Spring plunger devices 17, which are commercially available off-the-shelf items, are threadably mounted at diametrically opposed positions in threaded holes in the spring plunger collar 15 with each plunger 19 projecting upwardly therefrom to extend through each of two cooperating holes placed in the upper plate 10. A spring plunger device 17 comprises a threaded circular housing with a plunger spring mounted therein to project out of the top. These plungers 19 are threadably positioned in the threaded holes in spring plunger collar 15 to provide the required height above the upper plate 10, for a purpose to be hereinafter described.

A cam 42 is fixedly mounted on mounting tube 5, by a set screw A, below the spring plunger collar 15. A thrust washer 21 is positioned between a raised annular portion 23 on the top of the cam 42 and the annular bottom of the spring plunger collar 15. The thrust washer 21 provides a bearing surface between the top of annular portion 23 of movable cam 42 and the bottom stationary surface of spring plunger collar 15. Set screw A is in the raised annular portion 23. It can be seen that the mounting tube 5 is then axially held between the bottom of the recess 11 and the upper plate 10, while being permitted rotation.

The snubber, or attachment, mechanism 20 includes two rectangular slide members 36, each slidably mounted between two track members 38 fixed on the flat bottom 32 of the lower plate 12, one on each side of the mounting tube 5. An actuating flange 40 projects upwardly from the inner end of each rectangular slide member 36 to be actuated by the cam 42, and a snubber, or holding flange, 34 projects upwardly from the outer end of each rectangular slide member 36. Each holding flange 34 has its outer portion formed as a resilient pad 34A. The handle 29 is an indicator for the position of the snubber mechanism 20 so one preparing to use the I. V. stand 2 will know what position the holding flanges 34 are in. When the handle 29 is in the forward position, the snubber mechanism 20 is in the retracted position. When the handle 29 is in a position 90° to the side, the snubber mechanism 20 is in the fully extended position and also out of the way of the patient sitting in the wheelchair 22.

Cam 42, fixedly positioned on the mounting tube 5, has two diametrically opposed extending cam lobes 44 with reduced camming portions therebetween. Each cam lobe 44, when turned by the mounting tube 5, contacts an actuating flange 40 to move each holding flange 34 with its resilient pad 34A outwardly to press against a bar 48 of a wheelchair.

All standard wheelchairs 22 have a rearwardly extending fixed foot bar 48 at a height to be contacted by each of the holding flanges 34 and pads 34A. The common wheelchairs used in institutions are 16 inches and 18 inches, but there are other personal, or pediatric, chairs of varying foot bar distances. This variable snubber, or attachment, mechanism and flexibility of flanges 34 and 40 will accommodate different sizes. The height of the holding flange 34 with resilient pad 34A accommodates various heights of wheelchair foot bars 48. The flexibility of flanges 34 and 40 aids in accommodating varying widths between foot bars 48.

A detent collar 25 is fixedly mounted on mounting tube 5, by set screw B, above the upper plate 10. A narrow annular ring 25A extends downwardly from the bottom of the detent collar 25 around the center opening in the detent collar 25 to reduce the contact area to reduce friction between the rotating detent collar 25 and the flat top 30 of the upper plate 10. The detent collar 25 has detents 27 therein to be engaged by the plungers 19 at different positions to hold the cam 42, and therefore the holding flanges 34, at various predetermined distances apart. Stud 31 is mounted in spring plunger collar 15 to permit turning of the mounting tube 5 and connected I. V. pole 4 only 90°. The stud 31 extends downwardly and projects into a cam guide groove 31A in cam 42. Cam guide groove 31A covers a 90° arc in the cam 42. In one position of the cam 42, two spring plungers 19 align with two detents 27 in detent collar 25 to engage them and hold the I. V. pole handle 29 in its forward direction and the cam 42 in its retracted position.

Figure 7:
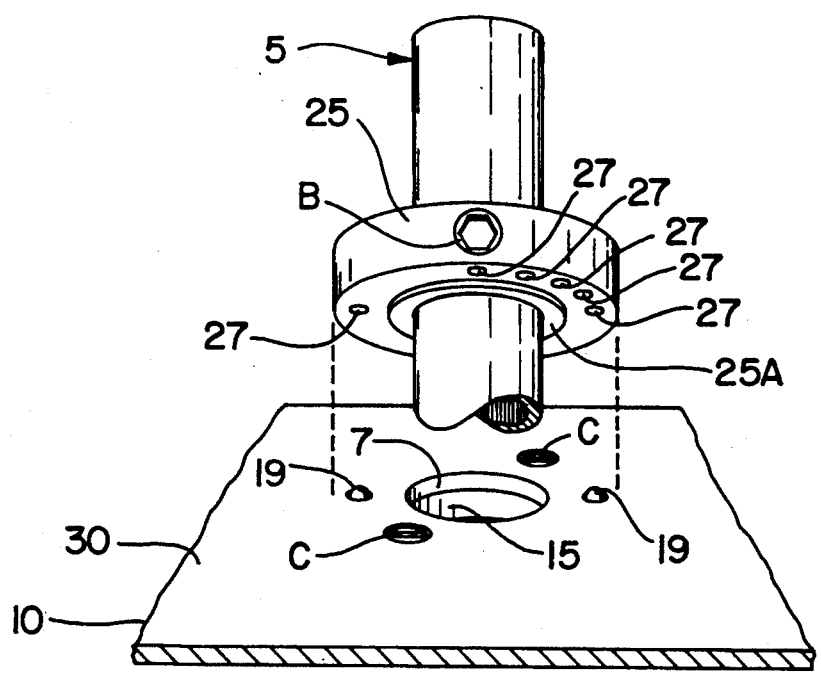
FIG. 7 is an exploded view of a portion of the upper plate of tile base with the mounting tube showing the positioning and holding mechanism for the mounting tube, I. V. pole and snubber, or holding flange, pads.
Figure 9:
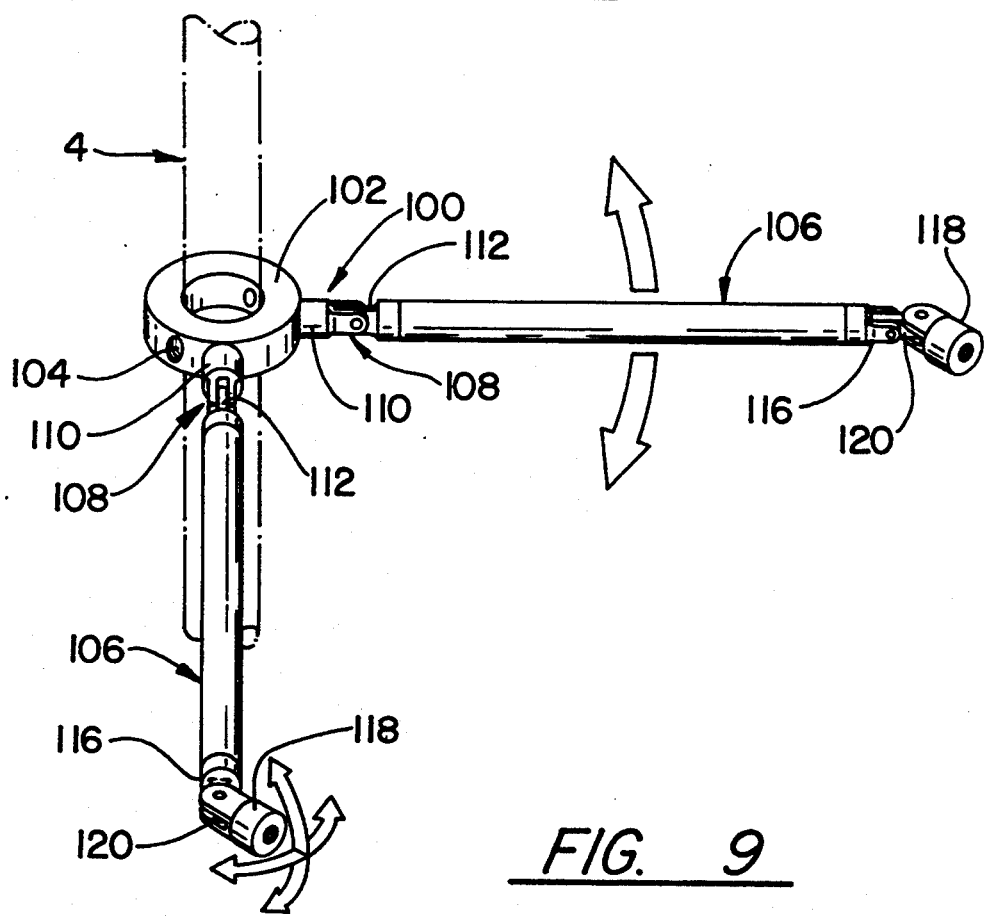
FIG. 9 is a perspective view of the attachment from the pole of the I. V. stand to the gurney.
Figure 8:
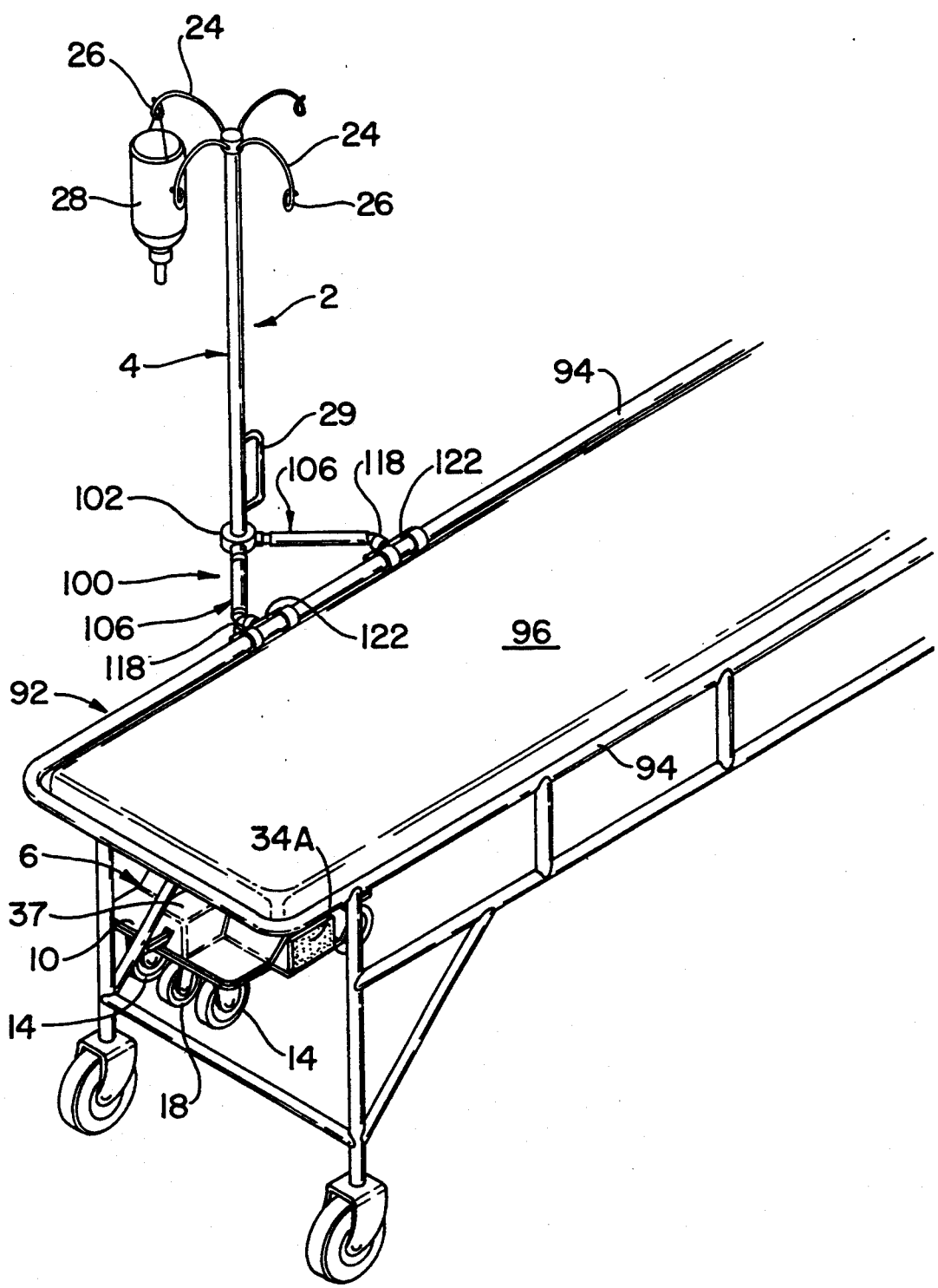
FIG. 8 is a perspective view of the I. V. stand attached to a gurney for moving therewith.
Figure 10:
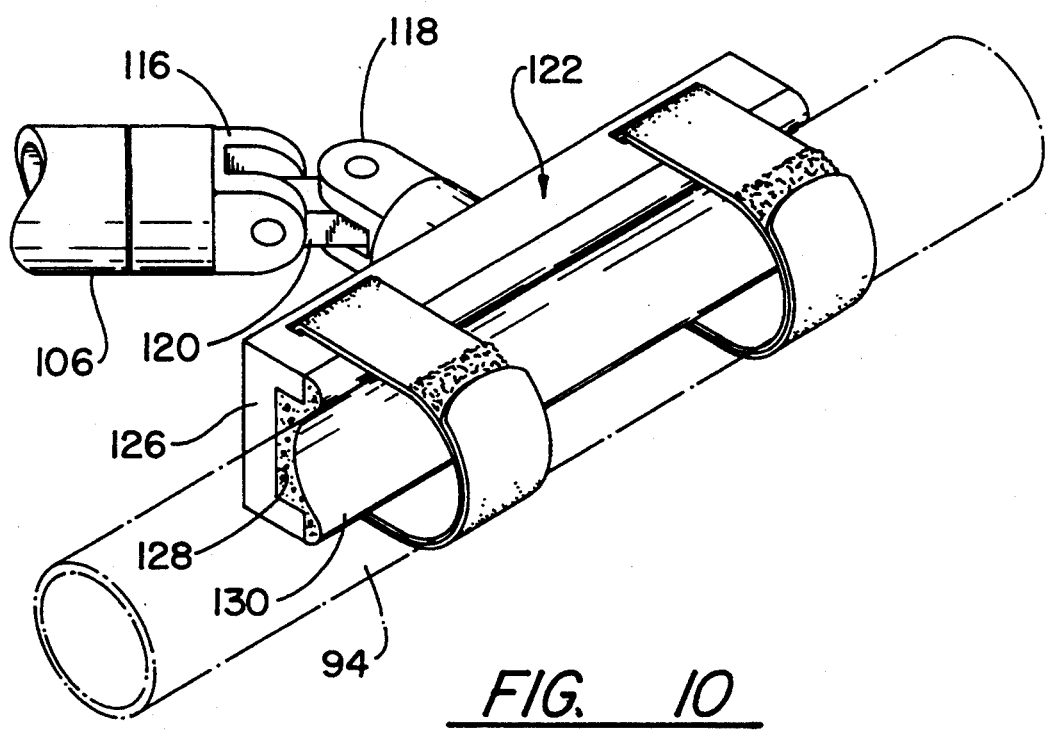
FIG. 10 is an enlarged view showing the attachment of an arm in FIG. 9 to a tube, or similar member, on a gurney.

When the mounting tube 5 and connected I. V. pole 4 are turned to move the cam lobes 44 inwardly from the actuating flanges 40, two springs 50, connected between the two actuating flanges 40, one on each side of mounting tube 5, pull the actuating flanges 40 inwardly against the surface of the cam 42 at all times. This action releases the holding flanges 34 and pad 34A from the foot bars 48 so as to be ready for the next outward cammed actuation. The springs are shown located below the cam 42 in FIG. 7A. Each rearwardly mounted stationary, or non-pivoted, wheel 14 is fixedly mounted in one of the two rear corners of the housing 8. Each wheel 14 is mounted in a forked wheel support 52 extending downwardly from a base plate which is fixed to the rear flat portions of upper and lower plates, 10 and 12, respectively. This can be done by bolts through openings 54 in the rear corners of the upper and lower plates, 10 and 12, respectively. Each forwardly mounted pivoted wheel 16 is castered and is pivotally mounted in one of the two forward corners of the housing 8. Each wheel 16 is mounted in a pivoted forked wheel support 56 providing caster alignment extending downwardly from a base plate which is fixed to the front flat portions of upper and lower plates 10 and 12, respectively. This can be done by bolts through openings 58 in the front corners of the upper and lower plates 10 and 12, respectively.

Figure 3:
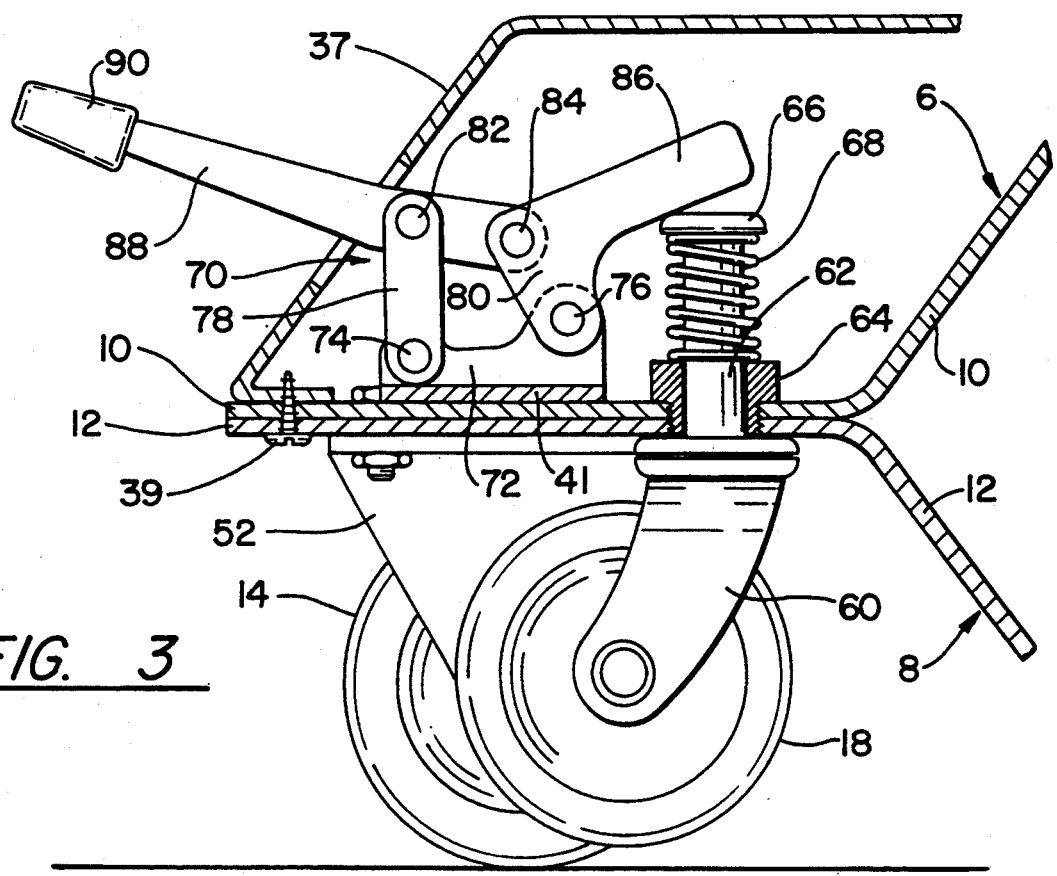
FIG. 3 is a fragmentary sectional view showing the fifth wheel mechanism of the I. V. stand in its retracted position.
Figure 4:
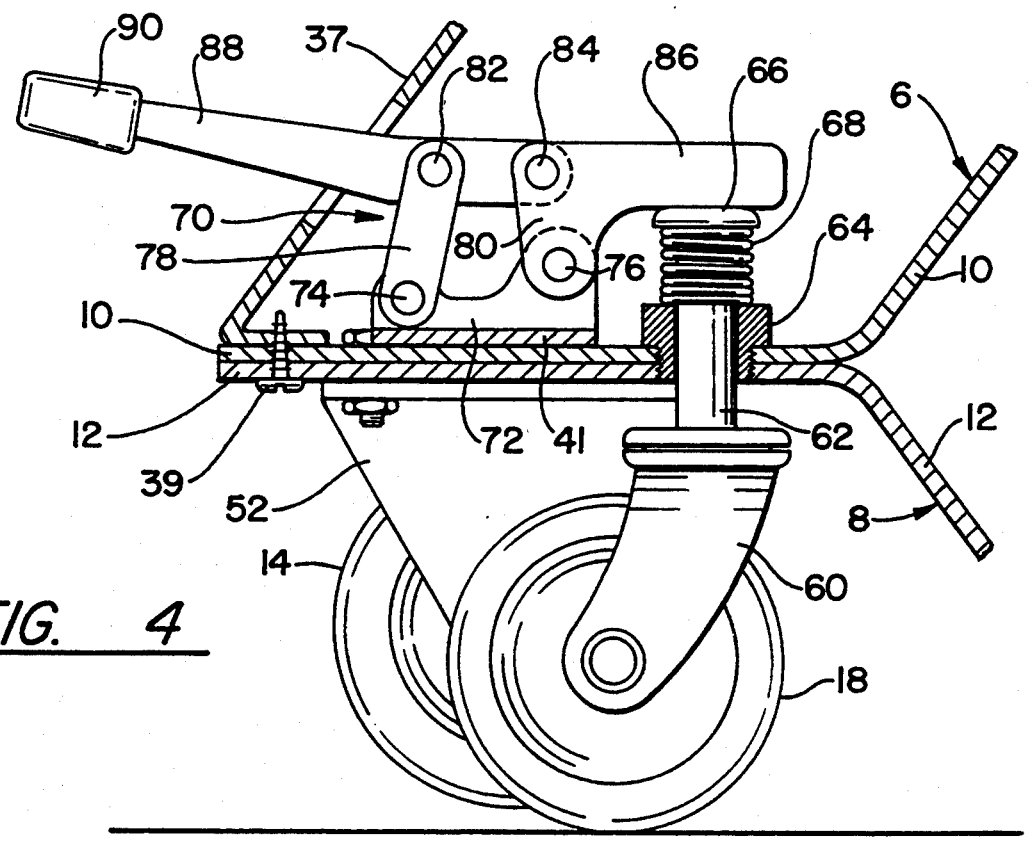
FIG. 4 is a fragmentary sectional view showing the fifth wheel mechanism of the I. V. stand in its extended position.
Figure 5:
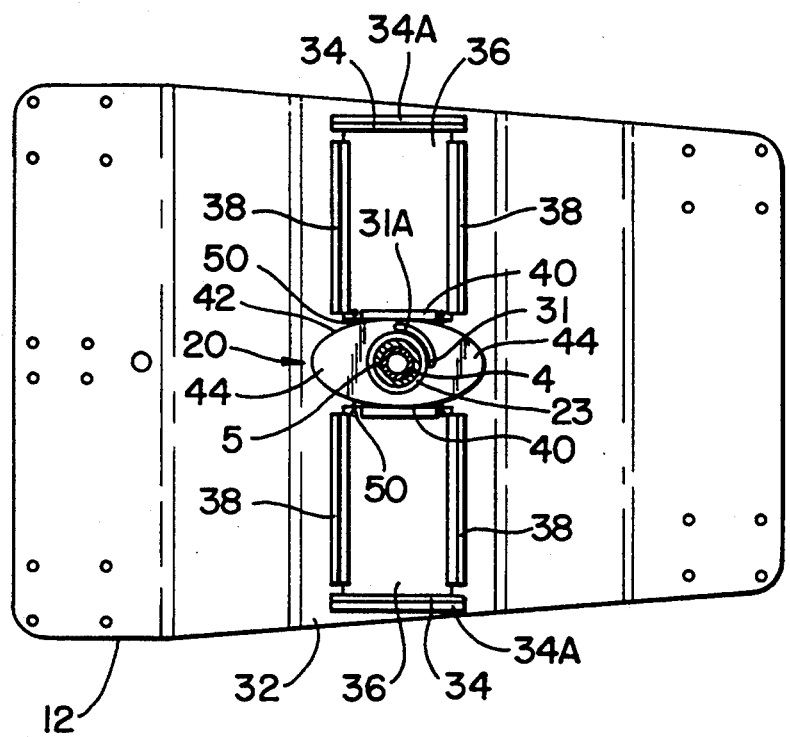
FIG. 5 is a top view of the wheelchair snubber, or attachment, mechanism in its retracted position below the upper plate, spring plunger collar, and thrust washer of the base.
Figure 6:
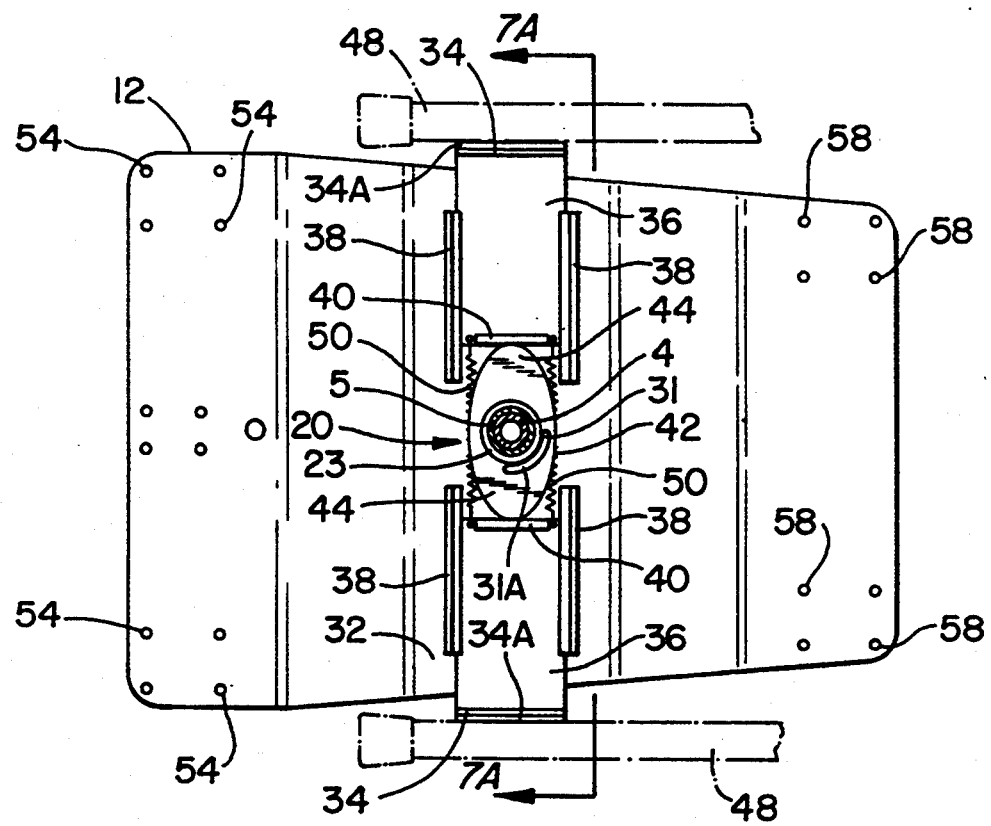
FIG. 6 is a top view of the wheelchair snubber mechanism in its extended position below the upper plate, spring plunger collar, and thrust washer of the base with snubber, or holding flange, pads pressed against bars on a wheelchair.

A fifth wheel 18 is mounted on said rear flat portion of upper and lower plates 10 and 12, respectively, between said non-pivoted wheels 14. A forked wheel support 60 providing caster has an upwardly extending shaft 62 pivotally and slideably mounted in a bushing 64. Bushing 64 is fixedly mounted to the upper and lower plates 10 and 12, respectively. Shaft 62 extends through said bushing for a predetermined distance and has an upper fixed flange 66. A spring 68 is mounted around said shaft 62 between the top of said bushing 64 and the bottom of said fixed flange 66 on said shaft 62. This action of spring 68 maintains the wheel 18 in an upward retracted position with the top of the forked wheel support 60 against the lower plate 12. The wheel 18 is smaller than the wheels 14, and the length of the forked wheel support 60 is of a length so that in the retracted position, the wheel 18 is off the floor a desired amount (see FIG. 3). The length of the shaft 62 is such that in a downward position of the fixed flange 66, it compresses spring 68 with the wheel 18 engaging the floor and lifting the rear stationary wheels 14 off the floor (see FIG. 4).

A foot-operated mechanism 70 is mounted on the upper plate 10 to engage the upper fixed flange 66 to move it to its down position placing the pivoted wheel 18 in its operating or extended position, engaging the floor and lifting the wheels 14 off the floor and locking it there. The foot-operated mechanism 70 has an upstanding flange 72 extending upwardly from a small base plate 41 which is fixed to the upper plate 10. The flange 72 has two fixed pivot points 74 and 76. Two links 78 and 80 are pivotably mounted at one end to the two fixed pivot points 74 and 76, respectively. Each of the links 78 and 80 has a movable pivot point 82 and 84, respectively, at its other end. Link 80 has an arm 86 extending from movable pivot point 84 over the upper fixed flange 66. An actuating foot lever 88 is pivotally connected to the two movable pivot points 82 and 84. A foot pad 90 is located on the free end of the actuating foot lever 88. The pivot points and linkages are arranged so that when the foot pad 90 is depressed, the arm 86 pushes the upper fixed flange 66 to its down position, locking it in that position. The actuating foot lever 88 is lifted to release the foot-operated mechanism 70 to allow the spring 68 to retract tile wheel 18 and permit the stationary wheels 14 to engage the floor. A cover 37 is located over the foot-operated mechanism 70 to keep it clean and prevent damage thereto. The cover 37 can be made of metal or plastic and it is fixed to the upper plate 10 of the base 6 by machine screws 39.

The intravenous, I. V., stand 2 can be attached to other patient conveyances such as gurneys 92. In the example shown, the gurney 92 is of the type having tubing rails 94 around the top of the gurney 92 adjacent the surface 96 on which the patient lies.

An attachment device 100 includes a collar 102 which can be fixed to a pole 4 by a lock screw 104. One or more lock screws 104 can be used. Two adjustable arms 106 are fixed to the collar 102. Each arm 106 is attached to the collar by a pivotal joint 108 which provides for "up and down" movement of each arm 106. The pivotal joints 108 are shown mounted to the collar 102 about 90° apart. Each pivotal joint 108 has a fork, or bifurcated part, 110, attached to the collar 102 with a cooperating tongue 112 fixed to the end of a connecting arm 106. Each tongue 112 is flat and pivotally affixed to its cooperating fork, or bifurcated, part 110 to permit "up and down" movement only.

Figure 11:
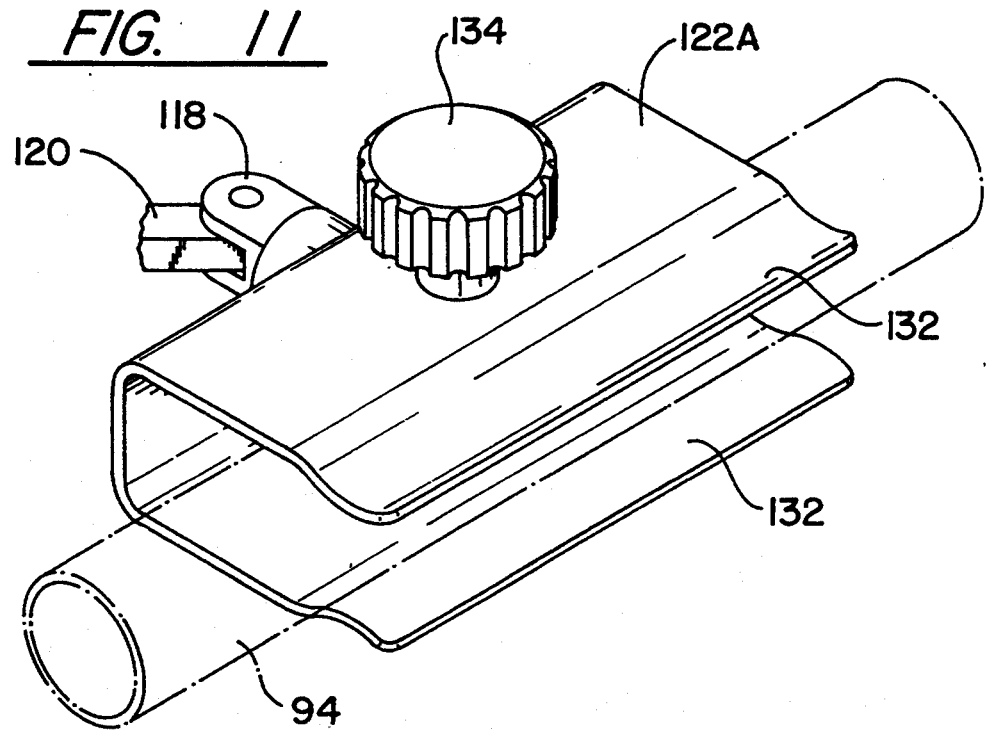
FIG. 11 s an enlarged view showing a modified attachment of an arm in FIG. 9 to a tube, or similar member, on a gurney.

A fork, or bifurcated part, 116 is fixed to the other end of each arm 106 with a fork, or bifurcated part, 118 adapted to be connected to the gurney 92. A link 120 is pivotally connected at one end to the fork 116 and at the other end to fork 118, forming a universal joint for movement in any direction. Fork, or bifurcated part, 118 is attached to a connecting device 122 which can be fixedly attached to a tube, or tubular rail, 94 on a gurney. The connecting device 122 comprises an elongated member 126 with a groove 128 along its length with rubber insert 130 fixed in the groove 128. The rubber insert 130 is fixed against a tube, or tubular rail, 94 by the use of a strip of cloth having Velcro at its ends, or some other connecting means. The rubber insert 130 can have a groove therein to match a tube, or tubular rail, 94. Other connecting devices can be used to fix a fork, or bifurcated part, 118 to a gurney, or other conveyance. A modified connecting device 122A is shown in FIG. 11 having an elongated clamp with elongated spring arms 132 with an operating screw knob 134 for tightening down on a tube, or pipe, 94. Knob 134 also loosens the connection.

While the principles of the invention have now been made clear in an illustrative embodiment, it will become obvious to those skilled in the art that many modifications in arrangement are possible without departing from those principles. The appended claims are, therefore, intended to cover and embrace any such modifications, within the limits of the true spirit and scope of the invention.

We claim:

1. An I. V. stand having an upstanding pole, a base, holding means on the pole for supporting medical objects, said base having five wheels, two of said wheels mounted on the front of said base for supporting said stand, two of said wheels mounted on the rear of said base for supporting said stand, said wheels mounted on the rear of said base being stationary, a fifth pivoted wheel having caster mounted on the rear of said base between said two stationary wheels, an extending and retracting mechanism for moving said fifth pivoted wheel downwardly to an extended position below said two stationary wheels for supporting said stand and moving said fifth pivoted wheel upwardly to a retracted position above said two stationary wheels for removing its support of said stand.

2. An I. V. stand as set forth in claim 1 wherein said extending and retracting mechanism has a foot operated mechanism for extending said fifth pivoted wheel downwardly to an extended position.

3. An I. V. stand as set forth in claim 2 wherein said foot operated mechanism provides means for holding said fifth pivoted wheel downwardly in its extended position when placed in that position.

4. An I. V. stand as set forth in claim 3 wherein said foot operated mechanism provides means for releasing said fifth pivoted wheel to be spring biased upwardly to its retracted position.

5. An I. V. stand having an upstanding pole means, a base, attachment means on said base for releasably attaching said I. V. stand to the rear of a wheelchair for movement therewith, said attachment means comprising holding flange means being movable outwardly on each side of said base for contacting a wheelchair to secure the I. V. stand to a wheelchair.

6. An I. V. stand as set forth in claim 5 wherein said base includes a housing, said housing being open on each side, said attachment means being located in said housing, said attachment means being movable to extend said holding flange means from the open sides of said housing to engage a wheelchair, said attachment means being movable by turning said pole means.

7. An I. V. stand as set forth in claim 6 wherein said attachment means includes a slide means on each side of said pole means in said housing, each slide means having an actuating member for moving each slide means outwardly to an extended position or inwardly to a retracted position, a cam means for moving said slide means outwardly, spring means for moving said slide means inwardly, means connecting said cam means to said pole means.

8. An I. V. stand as set forth in claim 7 including indicator means on said pole means to indicate the position of the attachment means.

9. An I. V. stand as set forth in claim 5 wherein said base has two rear non-pivoted wheels for supporting the rear of the base for straight movement, a swiveled wheel having caster, means mounting said swiveled wheel having caster between said two rear non-pivoted wheels for being extended to be below said non-pivoted wheels so that the swiveled wheel supports the rear of said base for movement in any direction or for being retracted to be above said non-pivoted wheels so that the non-pivoted wheels support the rear of said base.

10. An I. V. stand as set forth in claim 5 wherein said base has two rear non-pivoted wheels for supporting the rear of the base for straight movement, a swiveled wheel having caster, means mounting said swiveled wheel having caster between said two rear non-pivoted wheels for being extended to be below said non-pivoted wheels so that the swiveled wheel supports the rear of said base for movement in any direction for use with a wheelchair.

11. An attachment device for attaching an I. V. stand to a patient conveyance, said device having a collar for attachment to a pole on an I. V. stand, two adjustable arms, each adjustable arm having two ends, each adjustable arm being pivotally mounted at one end to said collar for "up and down" movement, each adjustable arm having a universal joint on the other end, each universal joint being fixed to a connecting device, each connecting device having means for fixedly connecting it to said patient conveyance.

12. An attachment device as set forth in claim 11 wherein said collar has two pivotal joints spaced approximately 90° apart around the collar, said pivotal joints being mounted for "up and down" movement for said adjustable arms.

* * * * *